United States Patent [19]

Protiva et al.

[11] 4,243,805

[45] Jan. 6, 1981

[54] 3-FLUORO-10-PIPERAZINO-8-SUBSTITUTED 10,11-DIHYDRODIBENZO-(BF) THIEPINS AND METHOD FOR THE PREPARATION THEREOF

[75] Inventors: Miroslav Protiva; Miroslav Rajšner; Karel Šindelář; Jiří Jílek; Václav Bártl; Jiřina Metyšová; Antonin Dlabač; Leon Langšádl; Josef Pomykáček; František Mikšik, all of Prague, Czechoslovakia

[73] Assignee: SPOFA, spojene podniky pro zdravotnickou vyrobu, Prague, Czechoslovakia

[21] Appl. No.: 972,323

[22] Filed: Dec. 22, 1978

[30] Foreign Application Priority Data

Dec. 22, 1977 [CS] Czechoslovakia ............... 8728/77

[51] Int. Cl.$^3$ .................. H61K 31/38; C07D 409/04
[52] U.S. Cl. ..................................... 544/375; 424/250
[58] Field of Search ...................... 544/375; 424/250

[56] References Cited

U.S. PATENT DOCUMENTS 3,966,737  6/1976  Gerecke et al. ................ 544/375

Primary Examiner—Jose Tovar

[57] ABSTRACT

Techniques for the preparation of 3-fluoro-10-piperazino-8-substituted 10,11-dihydrodibenzo-(b,f) thiepins and their addition salts with organic and inorganic acids are disclosed. The described compositions evidence psychotropic activity and low toxicity and are characterized as neuroliptics with a high degree of cataleptic, anti-apomorphine and central depressant action.

7 Claims, No Drawings

3 FLUORO-10-PIPERAZINO-8-SUBSTITUTED 10,11-DIHYDRODIBENZO-(b,f) THIEPINS AND METHOD FOR THE PREPARATION THEREOF

This invention relates to 8-substituted 10,11-dihydrodibenzo (b,f) thiepene derivatives. More particularly, the present invention relates to 3-fluoro-10-piperazino-8-substituted 10,11-dihydrodibenzo (b,f) thiepins and a method for preparation thereof.

The novel compositions described herein are of the general formula

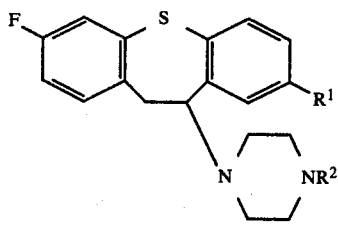 (1)

wherein
R$^1$ represents an alkyl group of 2–3 carbon atoms, a hydroxyl group, an ethoxyl group, an ethylthio group, NO$_2$, NH$_2$, CN, an aminocarbonyl group and an acyl group of 1–3 carbon atmos, and
R$^2$ is selected from the gourp consisting of C$_1$–C$_3$ alkyl groups, H, a hydroxyalkyl group of 2–3 carbon atoms, an acyloxyalkyl group of 4–20 carbon atoms wherein the acyl moiety is a part of an aliphatic or aromatic acid, a cyclic acetal radical of the formula

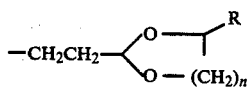

wherein R represents H or CH$_3$ and n ranges from 1–2, or wherein R represents a p-fluorophenylaliphatic radical of the general formula

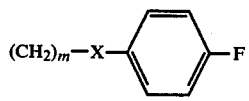

wherein m is an integer from 1–3, X represents a direct bond, oxygen or sulfur, a carbonyl group or a bivalent radical of the general formula

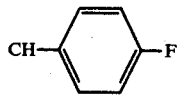

and the acid addition salts thereof.

The compositions described herein have been found to evidence psychotropic activity at acceptable levels of toxicity, so permitting use for therapeutic purposes. Additionally, the subject compositions are neuroleptic in nature and evidence a high degree of cataleptic, anti-apomorphine and central depressant action, such being superior to well known prior art compositions used for this purpose, for example, chlorpromazine, octoclothepin (8-chloro-10-(4-methylpiperazino)-10,11-dihydrodibenzo (b,f) thiepin. Studies have revealed that the novel compositions manifest a distinct prolongation of the time of action upon oral and parenteral administration. Thus, it has been found that the pharmacological effects subsist for a period of 48 hours and longer upon administration. This compares favorably with the above-mentioned prior art composition whose effect terminates 24 hours after administration. Still further, lipophilic esters of the described compositions when administered intramuscularly in the form of solutions in vegetable oils create a reservoir which is absorbed slowly, the effect thereof being detected several weeks after administration. In light of the fact that the parent amino alcohols, which represent the neuroleptically active part of the molecule of these esters, already possess a prolonged action, the intramuscular injection of the corresponding lipophilic esters represents a further prolongation of their effect, so yielding extraorinarily protracted action.

The compounds described herein may be prepared in accordance with several preparative procedures which are set forth hereinbelow:

(a) The most generalized technique for preparing the described compounds is a substitution reaction wherein chloro derivatives of the general formula

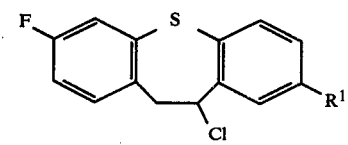 (2)

wherein R$^1$ is defined as in formula (1) with the exception of a hydroxyl and an amino group, are reacted with a piperazine derivative of the general formula

wherein R$^2$ is as defined in formula (1). This reaction may be effected by reaction of the chlorides with at least a 100% excess of the piperazine compound in boiling chloroform, the piperazine serving also as a condensation agent. This reaction may also be effected in the absence of a solvent by warming a mixture of the chloride with at least a 100% excess of the piperazine at a temperature ranging from 80°–120° C. Still a further procedure for effecting the substitution reaction involves the use of equimolar quantities of the chloride and piperazine, an appropriate condensation agent being employed also. Suitable agents for this purpose are triethylamine, pyridine or an alkali metal carbonate.

The substitution reaction may be conducted in an inert solvent, e.g., benzene, dimethylformamide or the like. It should also be noted that the chlorides employed are novel and have not been heretofore described in the iterature: their preparation is shown in the exemplary embodiments. Similarly, certain of the piperazines employed have not been described heretofore.

(b) The compounds of formula (1) may also be prepared by the reduction of the corresponding 10(11)-unsaturated compounds, namely, enamines of the general formula

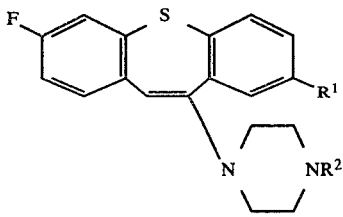

wherein $R^1$ is as described in formula (1) with the exception of easily reducible compounds, such as a nitro or acyl group, and $R^2$ is as described in formula (1) with the exception of the easily reducible p-fluorobenzoylalkyl radical.

The reduction of the enamines of formula (4) to the dihydro compounds of formula (1) may be effected with the use of various agents, for example, zinc in acetic acid, diboran liberated "in situ" by the reaction of sodium borohydride with acetic acid in tetrahydrofuran and the like. The described enamines of formula (4) are also novel compounds not heretofore reported in the literature. A method for their preparation is shown in the exemplary embodiments.

(c) Certain compounds of formula (1) may be prepared by the reduction of the corresponding amides of the general formula

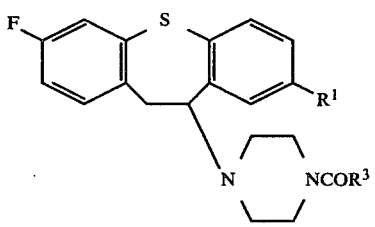

wherein $R^1$ is as defined in formula (1) with the exception of reducible groups, for example, a nitro, cyano, aminocarbonyl and acyl group, and $R^3$ is a radical shorter by a $CH_2$ group than $R^2$ of formula (1) with the exception of reducible groups, for example, an acyloxyalkyl and p-fluorobenzoylalkyl radical. Accordingly, this method is suitable for the preparation of those compounds of formula (1) wherein $R^2$ contains a methylene link attaching it to the nitrogen atom of the piperazine with the limitation to substitution by groups which do not contain any reducible moieties. Reduction of the amides of formula (5) requires the use of strong reducing agents, preferably complex metal hydrides such as lithium hydridoaluminate or sodium dihydrido-bis (2-methoxyethoxy) aluminate. This reduction is carried out either in diethyl ether, in other ether solvents such as tetrahydrofuran, diethyleneglycoldimethylether, or in aromatic hydrocarbons such as benzene, toluene or a xylene. In the event that the amide of formula (5) employed includes a $COOC_2H_5$ group as $R^3$, the reduction with the hydrides yields the respective methyl analog, that is, a compound of the formula (1) wherein $R^2$ is $CH_3$. Once again, the amides of formula (5) are novel compositions not heretofore described in the literature, method for the preparation thereof being set forth in the exemplary embodiments.

(d) Another method for the preparation of the compositions of formula (1) in which $R^2$ is hydrogen, that is, a secondary amine, involves hydrolysis of the amides of formula (5) wherein $R^1$ is defined as in formula (1) with the exception of easily reducible groups, for example, cyano or aminocarbonyl groups.

An alternative hydrolysis involves the use of an amide in the carbonate family of the general formula

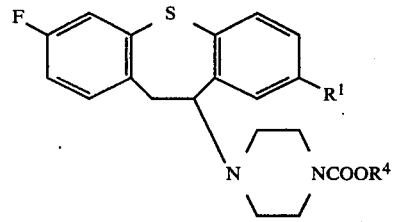

wherein $R^1$ is an defined in formula (1) with the exception noted above and $R^4$ is a lower alkyl group, preferably ethyl. The carbonates of formula (6) are also new compounds, the preparation of which is described in the exemplary embodiments. Their hydrolysis may be effected either with the use of acidic or alkaline agents. In the instant case, however, in light of the lability of the bond linking the skeletal carbon atom in position #10 with the piperazine $N^1$ nitrogen atom, a general preference exists for an alkaline hydrolysis. In order to effect this hydrolysis, severe conditions are required since the use of diluted ethanolic solutions of alkali metal hydroxides, especially potassium hydroxide, either does not yield the desired end or results in an unacceptable reaction rate. Accordingly, it is necessary to utilize high-boiling alcohols as solvents, diethyleneglycol and triethyleneglycol being found particularly suitable for this purpose. Alternatively, ethanolic potassium hydroxide solutions having concentrations of the order of 50% may be employed. The reaction mixture then attains substantially higher temperatures as compared with ethanol and the reaction proceeds rapidly and quantitatively.

(e) Another method for the preparation of the composition of formula (1) which is of general use involves the alkylation of the secondary amines of the general formula

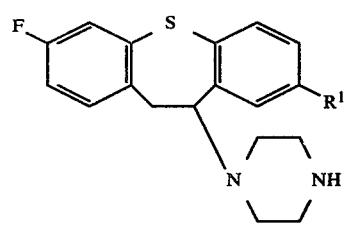

wherein $R^1$ is as defined in formula (1) with the exception of groups easily alkylated such as free amino and hydroxyl groups. The secondary amines of formula (7) are novel compounds and may be prepared in accordance with the procedure identified as (d) above. These compounds are considered to be within the scope of the instant invention, their preparation being specifically shown in the exemplary embodiments. Alkylation of the secondary amines of formula (7) may be effected by reaction with reactive esters of the general formula $$R^2—OH \qquad (8)$$

wherein $R^2$ is as defined in formula (1) with the exception of a hydrogen atom. Compounds suitable for this purpose include the corresponding chlorides, bromides, iodides, alkanesulfonates and arenesulfonates. Alkylation is effected by heating equimolar mixtures of the amines of formula (7) and the reactive esters of the alcohols of formula (8) in solvents such as ethanol, 1-butanol, dimethylformamide, etc. in the presence of up to a 100% excess of an anhydrous alkali metal carbonate, typically potassium carbonate.

(f) Esters of formula (1) wherein $R^2$ is an acyloxyalkyl group are preferred by the esterification of the amino alcohols of the general formula

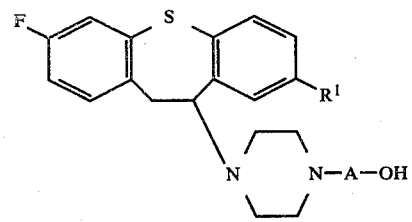

(9)

wherein $R^1$ is as defined in formula (1) with the exception of easily acylatable group that are readily acylated, for example, an amino group and an hydroxyl group, A representing a saturated hydrocarbon radical with a straight or branched chain of 2–3 carbon atoms. These amino alcohols are novel compounds which are considered to be within the scope of the invstant invention, the preparation thereof being set forth in the exemplary embodiments. Agents suitable for acylation or esterification are carboxylic acids of the general formula $$R^5\text{—COOH} \tag{10}$$

wherein $R^5$ is a hydrogen atom or an aliphatic or aromatic hydrocarbon radical of 1–17 carbon atoms or reactive derivatives thereof such as esters, halogenides or anhydrides. When free acids are employed, the esterification is found to proceed efficiently in a boiling aromatic hydrocarbon, benzene, toluene and the xylenes being found suitable for this purpose or under acidic catalysis, for example, in the presence of a small amount of p-toluenesulfonic acid with the continuous removal of reaction water by distillation in the form of an azeotropic mixture with the aromatic hydrocarbon employed.

When employing esters of the acids of formula (10), the reaction which occurs may be termed a transesterification. Esters of the lower alcohols, typically methanol or ethanol, are particularly suitable for this purpose, the reaction being effected under alkaline catalysis, preferably in the presence of a sodium alcoholate. These transesterification reactions are conveniently conducted in an aromatic hydrocarbon medium, the methanol and ethanol formed during the reaction being continuously distilled off together with the distillate of the hydrocarbon employed.

When using halogenides of the acids of formula (10), such as acid chlorides, the acylating agent is employed either in small excesses or in equivalent quantities, the reactions being conducted in a boiling inert solvent such as benzene or chloroform. The anhydrides of lower carboxylic acids of formula (10) are employed in excesses and the reaction is carried out in the absence of a solvent at temperatures ranging from 8°–150° C. Mixed anhydrides formed "in situ" may also be used for this purpose. Anhydrides of higher carboxylic acids are found unsatisfactory for the described acylation because of their comparatively low reactivity.

(g) A still further method for the preparation of the compounds of formula (1) is available when $R^1$ is OH. Suitable starting compounds for this purpose are ethers of the general formula

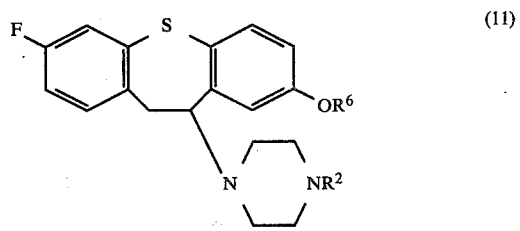

(11)

wherein $R^6$ is a lower alkyl or a benzyl group and $R^2$ is as defined in formula (1) with the exception of substituents which undergo cleavage during dealkylation reactions. The converstion of the ethers of formula (11) into the desired compounds of formula (1) wherein $R^1$ is OH is effected by dealkylation. When the $R^6$ group is a methyl or a lower alkyl group, the dealkylation is most conveniently performed with the use of boron tribromide in dichloromethane or chloroform. The intermediate compound initially formed is then subjected to alkaline hydrolysis to remove boron containing radicals and the products are isolated as the respective amphoteric substances or as "Zwitter" ions. This reaction and the products formed are contingent upon the simultaneous presence of basic amino moieties of the piperazine structure jointly with phenolic hydroxyl. When $R^6$ is a benzyl group, its elimination may be conveniently effected by reduction in an alkaline medium, for example, with the use of metallic sodium in 1-butanol. However, in the entirety of the cases under consideration, drastic acidic dealkylating agents and severe reaction conditions such as boiling with hydrobromic acid, heating with hydrochloric acid in a sealed tube or treatment with hydriodic acid, aluminum chloride or pyridine hydrochloride cannot be employed for the dealhylation since their energetic action produces an undesired decomposition by splitting the piperazine part of the molecule off the tricyclic skeleton.

(h) And lastly, a specific procedure for the preparation of compounds of formula (1) is employed when $R^1 = NH_2$. Suitable starting compounds in this case are nitro compounds of the general formula

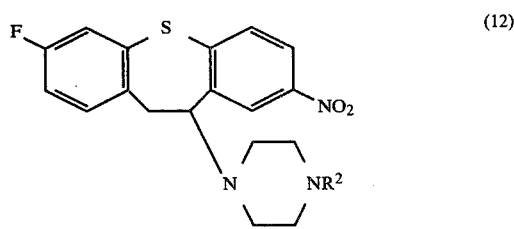

(12)

wherein $R^2$ is as defined in formula (1) with the exception of easily reducible groups such as a p-fluorobenzoylalkyl radical. The conversion of the nitro compounds of formula (12) into the compounds of formula (1) wherein $R^1$ is $NH_2$ may be effected by reduction, either by means of catalytic hydrogenation (typically with Raney nickel under mild reaciton conditions) or with the use of chemical reducing agents such as zinc or iron in the presence of acids or hydrazine in the presence of a ferric chloride catalyst as described in the exemplary embodiments. The starting nitro compounds of formula (12) are also considered an integral part of the present invention, their preparation being described in the exemplary embodiments.

The instant invention also is directed to the preparation of addition salts of the compounds of formular (1) and to thr compositions so produced. The salts are obtained by the neutralization of the bases with appropriate organic or inorganic acids in a suitable solvent, preferably in ethanol or in an ethanol-ether mixture. The resultant salts are typically easily crystallizable substances which are more convenient than the respective bases for conducting the pharmacological tests and preparing pharmaceutical dosages. Compositions including the compounds of formular (1) together with pharmaceutical excipients and/or auxiliaries.

The invention will be more fully understood by reference to the exemplary embodiments set forth hereinbelow. It will be appreciated that these examples are for purposes of exposition only and are not to be construed as limiting.

EXAMPLE 1

3-Fluoro-8-isopropyl-10-(4-methylpiperazino)-10,11-dihydrodibenzo (b,f) thiepin

A mixture of 3.9 g 10-chloro-3-fluoro-8-isopropyl-10,11-dihydrodibenzo (b,f) thiepin, 8 ml chloroform and 6.0 g 1-methylpiperazine was refluxed for 5 hours. After cooling, it was diluted with 100 ml of benzene and the solution washed several times with water. Next, it was shaken with an excess of 2% sulfuric acid. The separated sulfate of the product was filtered and added to the acid aqueous layer of the filtrate. The suspension was made alkaline with aqueous ammonia and the base extracted with benzene. The extract was then processed by drying with potassium carbonate and by evaporation yielding 4.3 g (70%) of an oily base. Its neutralization with maleic acid in ethanol and the addition of ether yielded a crystalline maleate with a m.p. of 174°–176° C.

The required 10-chloro-3-fluoro-8-isopropyl-10,11-dihydrodibenzo (b,f) thiepin is a new compound which has not heretofore been described in the literature. It may be obtained by the following synthetic procedure starting from the known 2-bromo-4-fluorophenylacetic acid (M. Rajsner et al., Collect. Czech. Chem. Commun. 42, 3079, 1977):

A mixture of 120 ml dimethylformamide, 66 g 2-bromo-4-fluorophenylacetic acid, 43.5 g 4-isopropylthiophenol (V. Valenta et al., Collect. Czech. Chem. Commun. 39, 783, 1974) and 6.6 g of copper powder was heated to 100° C. and treated at this temperature with 78 g of anhydrous potassium carbonate, added by parts under stirring. The mixture was then refluxed for 3.5 hours (bath temperature of 175°–180° C.). After partial cooling, the mixture was diluted with 350 ml water and the filtrate acidified with hydrochloric acid. The resulting 4-fluoro-2-(4-isopropylphenylthio) phenylacetic acid separated as an oil which was isolated by extraction with benzene. Processing of the extract yielded a residue which was dissolved in a mixture of 50 ml of cyclohexane and 200 ml of petroleum ether. Standing and cooling of this solution yields 38.2 g (45%) pure product, m.p. 115°–118° C.

Polyphosphoric acid was prepared form 30 ml 85% phosphoric acid and 45 g of phosphorus pentoxide. At 150° C., 8.5 g of 4-fluoro-2-2(4-isopropylphenylthio) phenylacetic acid were added to the pentoxide and the mixture stirred for 1 hour at the same temperature. After cooling, it was decomposed with 300 ml of ice-cold water and the product extracted with benzene. The extract was washed with a 5% sodium hydroxide solution and water, dried and evaporated. The slowly solidifying residue was then purified by crystallization from 13 ml ethanol. 3-Fluoro-8-isopropyldibenzo (b,f) thiepin-10(11H)-one was obtained in a yield of 5.9 g (74%) which in pure state melts at 76°–78° C.

A solution of 5.4 g of the noted ketone in 50 ml ethanol (prepared under heat and then cooled) was stirred and treated with 1.0 g of sodium borohydride in several portions. The mixture was then refluxed for 20 minutes and evaporated in vacuo. The residue was diluted with water and the product wxtracted with benzene. Processing of the extract yielded 5.9 g (90%) of the crystalline 3-fluoro-10-hydroxy-8-isopropyl-10,11-dihydrodibenzo(b,f) thiepin, which crystallized from cyclohexane and melted at 110°–112° C.

A boiling solution of 15.1 g of the foregoing alcohol in 40 ml benzene was then treated dropwise over 5 minutes with a solution of 7.2 ml thionyl chloride in 10 ml benzene. The mixture was refluxed for 1 hour and evaporated in vacuo. The residue was mixed with a small quantity of petroleum ether and filtered; 11.2 g (70%) 10-chloro-3-fluoro-8-isopropyl-10,11-dihydrodibenzo (b,f) thiepin were obtained, m.p. 82°–83° C.

EXAMPLE 2

3-Fluoro-10-[4-(2-hydroxyethyl)piperazino]-8-isopropyl-10,11-dihydrodibenzo (b,f) thiepin A mixture of 11.2 g 10-chloro-3-fluoro-8-isopropyl-10,11-dihydrodibenzo(b,f) thiepin (Example 1), 10.0 g 1-(2-hydroxyethyl)piperazine and 18 ml of chloroform were refluxed for 5 hours. After dilution with 100 ml of chloroform, the mixture was washed with water and the chloroform solution shaken with an excess of 3% sulfuric acid. The chloroform layer was separated and the aqueous one combined with the separated oily sulfate; this mixture was then made alkaline with aqueous ammonia. The separated base was extracted with other. Processing of the extract yielded 12.1 g (83%) of an oily base which was neutralized with maleic acid in ethanol. Addition of either separated the crystalline dimaleate, crystallizing from a mixture of 90% ethanol and ether as a hemihydrate melting at 98°–101° C.

EXAMPLE 3

3-Fluoro-10-[4-(3-hydroxypropyl)piperazino]-8-isopropyl-10,11-dihydrodibenzo (b,f) thiepin A mixture of 4.0 g 10-chloro-3-fluoro-8-isopropyl-10,11-dihydrodibenzo (b,f) thiepin (Example 1), 4.0 g 1-(3-hydroxypropyl) piperazine (T. Zawisa et al., Acta Polon. Pharm. 22, 477, 1965) and 7 ml of chloroform was refluxed for 5 hours and then processed in the manner described in Example 2. 4.4 g (76%) of an oily base which was converted to a crystalline dimaleate, m.p. 106°–108° C. (ethanol) was obtained.

EXAMPLE 4

3-Fluoro-8-isopropyl-10-piperazino-10,11-dihydrodibenzo(b,f)thiepin

A mixture of 3.07 g of 10-chloro-3-fluoro-8-isopropyl-10,11-dihydrodibenzo(b,f)thiepin (Example 1), 10 g of anhydrous piperazine and 20 ml chloroform was refluxed for 6 hours. Chloroform was then evaporated under reduced pressure, the residue dissolved in 100 ml of benzene and the solution wahsed thoroughly several times with water. It was then shaken with 100 ml 3 M-HCl. The benzene layer was separated and the aqueous one combined with the separated oily hydrochloride and made alkaline with aqueous ammonia; the base was isolated by extraction with benzene. PProcessing of the extract yielded 2.14 g (60%) of a crystalline base melting at 122°–124° C. (cyclohexane). Neutralization with maleic acide in 95% ethanol and the addition of ether yielded a crystalline maleate crystallizing from a mixture of 95% ethanol and ether as a hemihydrate, m.p. 162° C.

EXAMPLE 5

10-(4-Ethylpiperazino)-3-3fluoro-8-isopropyl-10,11-dihydrodibenzo(b,f)thiepin

A mixture of 3.07 g 10-chloro-3-fluoro-8-isopropyl-10,11-dihydrodibenzo(b,f)thiepin (Example 1), 5.0 g 1-ethylpiperazine (T. S. Moore et al., J. Chem. Soc. 1929, 39) and 8 ml of chloroform was refluxed for 5 hours. It was then processed as described in Example 1. 3.08 g (80%) of an oily base which was neutralized with maleic acid in ethanol affording the maleate was obtained. Recrystallization from ethanol yielded a pure substance melting at 201°–203° C.

EXAMPLE 6

3-Fluoro-8-isopropyl-10-(4-isopropylpiperazino)-10,11-dihydrodibenzo(b,f)thiepin A mixture of 3.07 g of 10-chloro-3-fluoro-8-isopropyl-10,11-dihydrodibenzo(b,f)thiepin (Example 1), 5.5 g of 1-isopropylpiperazino (A. B. Sen and K. shanker, J. Prakt. Chem. 302, 10, 1965) and 10 ml of chloroform was refluxed for 5 hours and then processed as in the foregoing cases. There was obtained 3.0 g (75%) of an oily base which yielded a crystalline maleate, m.p. 196°197.5° C. (ethanol).

EXAMPLE 7

3-Fluoro-10-[4-(4-fluorobenzyl)piperazino]-8-isopropyl-10,11-dihydrodibenzo(b,f)thiepin A mixture of 2.5 g of 10-chloro-3-fluoro-8-isopropyl-10,11-dihydrodibenzo(b,f)thiepin (Example 1), 3.2 g 1-(4-fluorobenzyl)piperazino and 7 ml of chloroform was refluxed for 8 hours. After dilution with chloroform, the solution was washed with water, dried with potassium carbonate and evaporated. The residue was chromatographed on a column of 150 g of alumina (activity II). Elution with chloroform yielded 3.1 g (82%) of a homogeneous oily base which yielded a crystalline dimaleate, m.p. 175° C. (acetone).

The required 1-(4-fluorobenzyl)piperazine has not heretofore been described in the literature. This compound may be obtained from the known 4-fluorobenzyl bromide (G. A. Oláh et al., J. Org. Chem. 22, 879, 1957) in the following manner.

A stirred solution of 34.6 g 1-(ethoxycarbonyl)piperazine in 50 ml dichloromethane is treated dropwise with a solution of 36.2 g 4-fluorobenzyl bromide in 50 ml of dichloromethane. The reaction is exothermic and the mixture is spontaneously heated to boiling (under reflux). The mixture is refluxed for 1 hour, a part of the dichloromethane distilled off and the residue treated with 50 ml of petroleum ether. There are separated 51 g (77%) of 1-(ethoxycarbonyl)-4-(4-fluorobenzyl)piperazine hydrobromide with a m.p. of 207°–208° C. (acetone). Treatment with aqueous ammonia releases the base which is isolated by extraction with benzene and purified by distillation, b.p. 184° C./2.5 Torr.

A mixture of 61 g of the foregoing base, 70 g potassium hydroxide and 75 ml of ethanol is stirred and heated under reflux in a bath of 120° C. After cooling, it is diluted with 50 ml of water and extracted with benzene. Processing of the extract yields 32 g (72%) 1-(4-fluorobenzyl)piperazine boiling at 108° C./2.3 Torr. The distillate solidifies to crystals melting at 64°–65° C. (petroleum ether).

EXAMPLE 8

3-Fluoro-10-(4-[2-(4-fluorophenyl)ethyl]piperazino)-8-isopropyl-10,11-dihydrodibenzo(b,f)thiepin A mixture of 3.0 g 10-chloro-3-fluoro-8-isopropyl-10,11-dihydrodibenzo(b,f)thiepin (Example 1), 4.1 g 1-[2-(4-fluorophenyl)ethyl]-piperazine and 7 ml of chloroform was refluxed for 8 hours and processed as in the foregoing case. Chromatography of the crude product on alumina yielded 2.2 g of a homogeneous oily base, which is transformed to the dimaleate, m.p. 171°–174° C. (acetone).

The required 1-[2-(4-fluorophenyl)ethyl]piperazone has not heretofore been described in the literature. It may be obtained from the known 2-(4-fluorophenyl)ethyl bromide (M. C. Suter and A. W. Weston, J. Amer. Chem. Soc. 63, 602, 1941) in the following manner:

A mixture of 80 g 1-(ethoxycarbonyl)piperazine and 41 g of 2-(4-fluorophenyl)ethyl bromide is kept at room temperature overnight and then heated to 100° C. for 1 hour. After cooling, it is diluted with 50 ml water and extracted with benzene. The extract is washed with water and then shaken with 5% hydrochloric acid. The separated solid hydrochloride is filtered off, washed with a small quantity of water, decomposed by treatment with aqueous ammonia and the base isolated again by extraction with benzene. Processing of the extract affords 51 g (91%) of the crude 1-(ethoxycarbonyl)-4-(2-[4-fluorophenyl]ethyl)piperazine, b.p. 198° C./3 Torr.

As in the foregoing Example, 48.6 g of the carbamate is hydrolyzed with 50 g potassium hydroxide in 50 ml ethanol at 120° C. Processing gives 21.5 g (60%) 1-[2-(4-fluorophenyl)ethyl]piperazine with a b.p. of 142° C./3 Torr. It may be transformed into a dimaleate crystallizing from 95% ethanol as a hemihydrate and melting at 164.5°–166.5° C.

EXAMPLE 9

3-Fluoro-10-(4-[2-(4-fluorophenoxy)ethyl]piperazino)-8-isopropyl-10,11-dihydrodibenzo(b,f)thiepin A mixture of 3.0 g of 10-chloro-3-fluoro-8-isopropyl-10,11-dihydrodibenzo(b,f)thiepin (Example 1), 5.0 g of 1-[2-(4-fluorophenoxy)ethyl]-piperazine and 10 ml of chloroform was refluxed for 8 hours and processed as in the foregoing cases. Chromatography of the crude product on alumina yields 3.6 g of a homogeneous oily base which may be transformed to the crystalline dimaleate, m.p. 155.5°–157.5° C.

The starting 1-[2-(4-fluorophenoxy)ethyl]piperazine is a new compound. It may be obtained in the following manner from two known compounds, namely 1-(2-chloroethyl)-4-(ethoxycarbonyl)piperazine (M. Harfenist, J. Amer. Chem. Soc. 76, 4991, 1954) and 4-fluorophenol (G. C. Finger et al., J. Amer. Chem. Sec. 81, 1959):

A mixture of 8.0 g of 4-fluorophenyl, 50 ml of acetone, 5 ml of water and 12.0 g of potassium carbonate was refluxed for 10 minutes and then treated dropwise with a solution of 18.4 g of 1-(2-chloroethyl)-4-(ethoxycarbonyl)piperazino hydrochloride in 20 ml of water. The mixture was diluted with 25 ml of acetone and refluxed under stirring for 7 hours. The main portion of the acetone was then evaporated under reduced pressure, the residue diluted with water and extracted with ether. The extract was washed with a 5% solution of sodium hydroxide and water, dried with potassium carbonate and evaporated. There were obtained 14.4 g (68%) of the crude 1-(ethoxycarbonyl)-4-[2-(4-fluorophenoxy)ethyl]piperazino, which is used in this state for further work.

A mixture of 13.3 g of the foregoing crude product, 15.0 g of potassium hydroxide and 15 ml of ethanol was heated under reflux for four hours in a bath at 120° C. After cooling, it was diluted with 20 ml of water and the product is extracted with benzene. The extract was washed with a saturated sodium chloride solution, dried with potassium carbonate, filtered with charcoal and the filtrate processed by distillation in vacuo. There were obtained 8.2 g (81%) of oily 1-[2-(4-fluorophenoxy)ethyl]piperazine with a b.p. of 125°–127° C./1.3 Torr.

EXAMPLE 10

3-Fluoro-10-(4-[2-(4-fluorophenylthio)ethyl]-piperazino)-8-isopropyl-10,11-dihydrodibenzo(b,f)thiepin A mixture of 3.0 g of 10-chloro-3-fluoro-8-isopropyl-10,11-dihydrodibenzo(b,f)thiepin (Example 1), 6.0 g of 1-[2-(4-fluorophenylthio)ethyl]piperazino and 10 ml of chloroform was refluxed for 8 hours and processed as in the foregoing cases. Chromatography of the crude product on a column of alumina yielded 4.0 g of a homogeneous oily base which was transformed to the crystalline maleate, m.p. 184°–186.5° C.

The required 1-[2-(4-fluorophenylthio)ethyl]-piperazino has not yet heretofore been described in the literature. It may be obtained in the following manner from two known starting compounds, namely 1-(2-chloroethyl)-4-(ethoxycarbonyl)piperazino (cf. Example 9) and 4-fluorothiophenol (M. Rajsner et al., Cesk. Farm. 11, 451, 1962).

Potassium carbonate (20.0 g) is added to a solution of 12.8 g of 4-fluorothiophenol in 200 ml acetone and the mixture refluxed under stirring for 20 minutes. There are then added 25.7 g 1-(2-chloroethyl)-4-(ethoxycarbonyl)piperazino hydrochloride and the refluxing continued for an additional 13 hours. The undissolved inorganic salts are then removed by filtration and washed with acetone and the filtrate evaporated. The residue is next dissolved in ether, the product transferred into an aqueous layer by shaking with an excess of dilute hydrochloric acid and from the solution of the hydrochloride, the base is released again by making it alkaline with a 20% sodium hydroxide solution. The product is isolated by extraction with ether. Processing of the extract yields 26.4 g (85%) crude 1-(ethoxycarbonyl)-4-[2-(4-fluorophenylthio)ethyl]piperazine, a sample of which distills at 205° C./2 Torr.

A mixture of 5.0 g of the foregoing compound, 5.0 g of potassium hydroxide and 5 ml of ethanol was heated under reflux with stirring for 3 hours in a bath at 120° C. After cooling, it was diluted with 10 ml of water and extracted with benzene. The extract was dried with potassium carbonate and benzene evaporated therefrom. The residue was then dissolved in 30 ml of ethanol and the solution neutralized with 4.4 g of maleic acid in 10 ml of ethanol. Standing overnight leads to separation of 7.0 g 1-[2-(4-fluorophenylthio)ethyl]-piperazino dimaleate hemihydrate which crystallized from 95% ethanol and melted at 143°–145° C. Decomposition of this salt with aqueous ammonia and extraction with ether affords an oily base which is used for further work.

EXAMPLE 11

3-Fluoro-10-(4-[3-(4-fluorobenzoyl)propyl]piperazino)-8-isopropyl-10,11-dihydrodibenzo(b,f)thiepin A mixture of 3.0 g of 10-chloro-3-fluoro-8-isopropyl-10,11-dihydrodibenzo(b,f)thiepin (Example 1), 5.3 g of 1-3-(4-fluorobenzoyl)propyl piperazine (M. Rajsner et al., Collect. Czech. Chem. Commun. 40, 1218 1975) and 10 ml of chloroform was refluxed under stirring for 8 hours. It was then diluted with 100 ml of chloroform and washed with a solution of 1.0 g of sodium hydroxide in 100 ml of water. The chloroform solution was then separated, dried with potassium carbonate and chromatographed on a column of 150 g alumina (act.II). Petroleum ether was used to elute the less polar impurities and benzene then eluted 3.57 g (70%) of a homogeneous base crystallizing from acetone and melting at 104°–106° C. Neutralization with maleic acid yielded a dimaleate crystallizing from acetone and melting in pure state at 145°–147° C.

EXAMPLE 12

3-Fluoro-10-(4-[4,4-bis(4-fluorophenyl)butyl]-piperazino)-8-isopropyl-10,11-dihydrodibenzo(b,f)thiepin A mixture of 2.5 g of 10-chloro-3-fluoro-8-isopropyl-10,11-dihydrodibenzo(b,f)thiepin (Example 1), 5.5 g of 1-[4,4-bis(4-fluorophenyl)-butyl]piperazino (L. Levai, Hung. Teljes 227; Chem. Abstr. 74, 42 386, 1971) and 7 ml of chloroform was refluxed for 5 hours. After cooling, it was diluted with water and extracted with chloroform. The crude product obtained by processing of the extract was chromatographed on a column of 150 g alumina (act.II). Benzene eluted in the first fractions the less polar impurities which were followed by 3.9 g of a homogeneous oily base. Neutralization with maleic acid in ethanol yielded a maleate which crystallized from 95% ethanol as a dihydrate which melts at 185°–187° C.

EXAMPLE 13

10-(4-2-(1,3-Dioxolan-2-yl)ethyl piperazino)-3-fluoro-8-isopropyl-10,11-dihydrodibenzo(b,f)thiepin A mixture of 3.0 g of 10-chloro-3-fluoro-8-isopropyl-10,11-dihydrodibenzo(b,f)thiepin (Example 1), 6.0 g of 1-[2-(1,3-dioxolan-2-yl)-ethyl]piperazino (cf. M. Protiva et al., Czech. 156.878) and 15 ml of chloroform was refluxed for 8 hours. Chloroform was then evaporated, the residue decomposed with water and extracted with benzene. The extract was thoroughly washed with water, dried with potassium carbonate and evaporated. There were obtained 4.0 g of a crude oily base which was neutralized with maleic acid in ethanol and yielded

EXAMPLE 14

10-[4-(2-Acetoxyethyl)piperazino]-3-fluoro-8-isopropyl-10,11-dihydrodibenzo(b,f)thiepin A mixture of 3.0 g of 10-chloro-3-fluoro-8-isopropyl-10,11-dihydrodibenzo(b,f)thiepin (Example 1), 4.0 g of 1-(2-acetoxyethyl)piperazino (cf. D. C. Kriesel and O. Gisvold, J.Pharm. Sci. 56, 325, 1967) and 10 ml of chloroform was refluxed for 8 hours. After cooling, it was decomposed with water and extracted with chloroform. The extract was then thoroughly washed with water, dried and evaporated. There were obtained 4.5 g of a crude oily base which was neutralized with maleic acid in acetone. The dimaleate was obtained which crystallized from acetone and melted at 153°–155.5° C.

EXAMPLE 15

10-[4-(2-Decanoyloxyethyl)piperazino]-3-fluoro-8-isopropyl-10,11-dihydrodibenzo(b,f)thiepin A mixture of 3.0 g of 10-chloro-3-fluoro-8-isopropyl-10,11-dihydrodibenzo(b,f)thiepin (Example 1), 6.0 g of 1-(2-decanoyloxyethyl)piperazino and 10 ml of chloroform was refluxed for 7 hours. After dilution with benzene, the solution was shaken with a saturated solution of potassium hydrogen carbonate and water, dried with potassium carbonate and evaporated. The viscous residue was dissolved in a small quantity of benzene and the solution chromatographed on a column of 140 g alumina (act.II). Benzene eluted first a small quantity of a less polar impurity which was followed by 2.8 g of the required homogeneous ester which was oily. Neutralization with maleic acid in acetone yielded the dimaleate crystallizing from acetone and melting in the pure state at 112°–113° C.

The required starting 1-(2-decanoyloxyethyl)-piperazino was obtained from the known 1-benzyl-4-(2-hydroxyethyl)piperazino (Y. Ikeda et al, Yakugaku Zasshi 89, 669, 1969; R. Baltzly et al., J. Amer. Chem. Soc. 66, 263, 1944) by application of the procedure described for the preparation of the homologous 1-(3-decanoyloxypropyl)piperazino (I. Cervena et al., Collect. Czech. Chem. Commun. 41, 3437, 1976). The substance is used for further work as the crude product, i.e. the oily residue after the evaporation of the solvent.

EXAMPLE 16

3-Fluoro-8-isopropyl-10-(4-[2-(3,4,5-trimethoxybenzoyloxy)ethyl]piperazino)-10,11-dihydrodibenzo(b,f)-thiepin A mixture of 3.0 g 10-chloro-3-fluoro-8-isopropyl-10,11-dihydrodibenzo(b,f)thiepin (Example 1), 6.5 g 1-[2-(3,4,5-trimethoxybenzoyloxy)ethyl]piperazino and 10 ml of chlorofrom was processed as in the previous case. There were obtained 4.5 g of crude base which was neutralized with oxalic acid in ethanol giving an oxalate which crystallized from aqueous ethanol and melted at 188°–192° C. under decomposition.

The crude 1-[2-(3,4,5-trimethoxybenzoyloxy)ethyl]-piperazino was obtained in the same manner as in the corresponding intermediate in the previous case from the known 1-benzyl-4-(2-hydroxyethyl)piperazino by esterification with 3, 4, 5-trimethoxybenzoyl chloride and by the following catalytic debenzylation by hydrogenolysis on palladium.

EXAMPLE 17

8-Ethyl-3-fluoro-10-(4-methylpiperazino)-10,11-dihydrodibenzo(b,f)thiepin

A mixture of 9.4 g of 10-chloro-8-ethyl-3-fluoro-10,11-dihydrodibenzo(b,f)thiepin, 10 g of 1-methylpiperazine and 15 ml of chloroform was refluxed for 8 hours. After evaporation of chloroform, the residue was decomposed with water and extracted with benzene. The extract was washed with water and shaken with 75 ml 3 M-HCl. The separated solid hydrochloride was filtered after 30 minutes of standing and washed with benzene. It was suspended in 150 ml of water; treatment with aqueous ammonia released the base which was isolated again by extraction with benzene. Processing of the extract yields 8.3 g (72%) of an oily base. Neutralization with maleic acid in ethanol and addition of ether precipitated the maleate which crystallized from a mixture of ethanol and ether and melts in the pure state at 156° C.

The starting 10-chloro-8-ethyl-3-fluoro-10,11-dihydrodibenzo(b,f)-thiepin is a new compound which may be prepared by the following synthesis starting from the known 2-amino-4-fluorotoluene (M. Rajsner et al., Collect. Czech. Chem. Commun. 40, 719, 1975):

2-Amino-4-fluorotoluene (68 g) is added dropwise to a stirred solution of 100 ml hydrochloric acid in 700 ml of water and after cooling to 0°–5° C., a solution of 46 g sodium nitrite in 100 ml water was slowly added dropwise. The resultant ice-cold solution of the diasonium chloride was added over 1 hour with stirring to a solution of 157 g potassium iodide and 35 ml of sulfuric acid in 250 ml water at 20°–25° C. The mixture was then stirred and heated for 2 hours at 100° C. After cooling, an oily product was separated and the remaining aqueous layer extracted with benzene. The separated product was dissolved in the benzene layer, the solution washed with a 5% sodium hydrogen sulfite solution, with water, 5% sodium hydroxide solution and again with water, dried with magnesium sulfate and filtered with charcoal. From the filtrate, benzene was evaporated under reduced pressure and the residue distilled. There were obtained 105.3 g of 2-iodo-4-fluorotoluene boiling at 92°–95° C./17 Torr.

A solution of 23.6 g of 2-iodo-4-fluorotoluene in 50 ml of tetrachloromethane was treated with 0.2 g of dibenzoyl peroxide and 19.6 g of N-bromosuccinimide. The mixture was then refluxed for 6 hours and illuminated by a 200 W bulb. After cooling, the spearated succinimide was filtered off and washed with 15 ml tetrachloromethane. The filtrate was evaporated and the residue distilled. There was obtained 24.8 g of 4-fluoro-2-iodobenzyl bromide with a b.p. of 130°–140° C./20 Torr. The product crystallized on standing and a sample recrystallized from petroleum ether; m.p. 71°–73° C.

A solution of 59 g of the foregoing bromide in 150 ml of dimethylformamide was treated with 27.6 g sodium cyanide and the mixture heated with stirring to 100°–110° C. for 8 hours. After cooling, the separated sodium bromide was filtered off, washed with 30 ml of dimethylformamide and the filtrate evaporated under reduced pressure. The residue was diluted with 1 liter of water and the separated product isolated by extraction with benzene. The extract was washed with water, dried with magnesium sulfate and filtered with charcoal. The filtrate was evaporated under reduced pressure. Distillation yielded 39.6 g (80%) (4-fluoro-2-iodophenyl)acetonitrile, b.p. 160° C./20 Torr. The distillate solidified and a sample recrystallized from a mixture of benzene and petroleum ether; m.p. 52°–53° C.

A solution of 41.5 g of potassium hydroxide in 170 ml water was added to a solution of 38.5 g of the foregoing nitrile in 200 ml of ethanol and the mixture refluxed for 12 hours. After evaporation of ethanol, the residue was treated with 400 ml water. The resultant solution was washed with benzene and filtered with charcoal. The filtrate was then acidified with a 1:1 dilute hydrochloric acid. (4-Fluoro-2-iodophenyl)acetic acid, separated by standing overnight, was filtered, washed with water and dried in vacuo. It was obtained in a yield of 34 g (82%) and melted at 112°–114° C. In this state, it was sufficiently pure for further work. Crystallization of a sample from aqueous ethanol yielded the pure substance melting at 114°–115° C.

4-Ethylthiophenol (K. Pelz and M. Protiva, Collect. Czech. Chem. Commun. 32, 2161, 1967) (10.4 g) was added to a solution of 14 g of potassium hydroxide in 120 ml water and after 10 minutes of stirring, the mixture treated with 21 g of (4-fluoro-2-iodophenyl)acetic acid and 2 g of freshly prepared copper powder. The mixture was stirred and refluxed for 7 hours. The hot mixture was filtered with charcoal and the cooled filtrate acidified with 30 ml of a 1:1 dilute hydrochloric acid. The separated oily [2-(4-ethylphenylthio)-4-fluorophenyl]acetic acid was separated by decantation of the aqueous layer which was substituted by pure ice-cold water. The product then crystallized quickly. It was filtered after standing overnight, washed with water and dried. The crystalline acid was obtained in a yield of 16.0 g (74%). It crystallized from aqueous ethanol and melted in the pure state at 108°–109° C.

A mixture of 14.5 g of the foregoing acid, 200 g polyphosphoric acid and 100 ml toluene was stirred and refluxed for 7 hours in a bath of 130°–135° C. After cooling, it was decomposed with ice and water and extracted with toluene. The extract was washed with 150 ml 5% sodium hydroxide solution, dried with potassium carbonate and evaporated. The residue was the crude 8-ethyl-3-fluorodibenzo(b,f)-thiepin-10(11)-one in a yield of 11.2 g (83%) which crystallized from ethanol and melted in a pure state at 74° C.

A solution of 10 g of the foregoing ketone in 150 ml ethanol was stirred and treated over 20 minutes at 70° C. with a solution of 2.8 g sodium borohydride in 20 ml water containing 1 ml 5% sodium hydroxide solution. The mixture was refluxed for 5 hours and ethanol evaporated under reduced pressure. The residue decomposed with water and the product extracted with benzene. The crude 8-ethyl-3-fluoro-10,11-dihydrodibenzo(b,f)thiepin-10-ol was obtained in an almost theoretical yield (10 g). After crystallization from cyclohexane, the substance was pure and melted at 97° C.

Powdered anhydrous calcium chloride (9 g) was added to a solution of 9.4 g of the foregoing alcohol in 120 ml of benzene and the suspension saturated over 2 hours under stirring with anhydrous hydrogen chloride. After 1 hour standing, the mixture was filtered, and the filtrate evaporated under reduced pressure. The required 10-chloro-8-ethyl-3-fluoro-10,11-dihydrodibenzo(b,f)thiepin was obtained in an almost theoretical yield (10.0 g); crystallization from petroleum ether yielded the pure substance melting at 68°–70° C.

EXAMPLE 18

8-Ethoxy-3-fluoro-10-(4-methylpiperazino)-10,11-dihydrodibenzo(b,f)thiepin

As in the foregoing case, a reaction of 8.4 g 8-ethoxy-3-fluoro-10-chloro-10,11-dihydrodibenzo(b,f)thiepin with 10 g 1-methylpiperazine in 15 ml boiling chloroform was carried out. There was obtained 6.8 g (67%) of an oily base which was transformed by neutralization with maleic acid in ethanol and by the addition of ether to the crystalline maleate with a m.p. of 130°–131° C. (ethanol-ether).

The starting 10-chloro-8-ethoxy-3-fluoro-10,11-dihydrodibenzo(b,f)thiepin (m.p. 110°–111° C., crystals from ethanol) was obtained in the manner described for the analogous compound in the foregoing Example, i.e., starting from (4-fluoro-2-iodophenyl)acetic acid (cf. the foregoing Example) via

[2-(4-Ethoxyphenylthio)-4-fluorophenyl]acetic acid, m.p. 108° C. (aqueous ethanol);
8-Ethoxy-3-fluorodibenzo(b,f)thiepin-10(11H)-one, m.p. 107°–108° C. (ethanol);
8-Ethoxy-3-fluoro-10,11-dihydrodibenzo(b,f)thiepin-10-ol, m.p. 81°–82° C. (cyclohexane).

EXAMPLE 19

8-(Ethylthio)-3-fluoro-10-(4-methylpiperazino)-10,11-dihydrodibenzo(b,f)thiepin

As in the foregoing cases, the reaction of 6.2 g of 10-chloro-8-(ethylthio)-3-fluoro-10,11-dihydrodibenzo(b,f)thiepin with 7 g of 1-methylpiperazine in 12 ml of boiling chloroform was carried out. There were obtained 5.9 g (80%) of an oily base, yielding by neutralization with maleic acid in ethanol and by the addition of ether the crystalline maleate, melting in pure state at 124°–125° C. (ethanol-ether).

The starting 10-chloro-8-(ethylthio)-3-fluoro-10,11-dihydrodibenzo(b,f)thiepin (m.p. 110° C., crystals from cyclohexane) was prepared in the manner described for analogous compounds in the foregoing Examples, i.e., from (4-fluoro-2-iodophenyl)acetic acid (cf. Example 17) via

[2-(4-Ethylthiophenylthio)-4-fluorophenyl]acetic acid, m.p. 99° C. (aqueous ethanol);
8-(Ethylthio)-3-fluorodibenzo(b,f)thiepin-10(11H)-one, m.p. 82° C. (ethanol);
8-(Ethylthio)-3-fluoro-10,11-dihydrodibenzo(b,f)thiepin-10-ol, m.p. 104°–105° C. (cyclohexane).

EXAMPLE 20

3-Fluoro-10-[4-(2-hydroxyethyl)piperazino]-8-nitro-10,11-dihydrodibenzo(b,f)thiepin A mixture of 6.7 g of 10-chloro-3-fluoro-8-nitro-10,11-dihydrodibenzo(b,f)thiepin, 15 ml of 1-(2-hydroxyethyl)piperazine and 20 ml of acetonitrile was refluxed for 3 hours. After cooling, it was decomposed with water and extracted with benzene. The extract was shaken with an excess of 10% hydrochloric acid, the separated hydrochloride filtered off and combined with the aqueous layer of the filtrate. The suspension was then made alkaline with 20% sodium hydroxide solution and the base isolated by extraction with a mixture of ether and benzene. Processing of the extract yielded 5.9 g of an oily base which was neutralized with maleic acid in acetone. Addition of ether separated the crystalline bis(hydrogen maleate) which recrystallized from a mixture of acetone and ether, m.p. of the pure substance is 75°–78° C. Decomposition of the maleate with aqueous ammonia and extraction with ether yielded the pure base which likewise was crystalline, m.p. 134°–137° C. (ethanol).

The starting 10-chloro-3-fluoro-8-nitro-10,11-dihydrodibenzo(b,f)thiepin was obtained by the following synthesis from the known (4-fluoro-2-nitrophenyl)acetic acid (K. Sasajima et al, Japan, Kokai 72/38.947; Chem. Abstr. 78, 58 051u, 1973):

(4-Fluoro-2-nitrophenyl)acetic acid (80 g) was dissolved in a solution of 16.0 g sodium hydroxide in 500 ml water and the solution hydrogenated in the presence of 8.0 g of a 10% palladium catalyst on charcoal under normal pressure and at room temperature on a shaker. After attaining the theoretical consumption of hydrogen, the catalyst was removed by filtration and the filtrate evaporated in vacuo to dryness. There were obtained 76 g of a practically pure sodium salt of (2-amino-4-fluorophenyl)acetic acid.

The noted sodium salt (30 g) was dissolved together with 11.7 g of sodium nitrite in 50 ml water and the solution slowly added dropwise to a mixture of 70 ml hydrochloric acid and 70 g ice at a temperature not surpassing 5° C. It was stirred under cooling for 1 hour and the ice-cold solution of the diazonium salt added dropwise with stirring over 15 minutes to a solution of 58 g of sodium sulfide nonahydrate, 6.4 g of sulfur and 8.0 g of sodium hydroxide in 70 ml water. The mixture was finally made alkaline with the required quantity of 20% sodium hydroxide solution and stirred for 2.5 hours. After acidification with 40 ml hydrochloric acid, the separated substance was filtered, added to a solution of 15 g of sodium carbonate in 500 ml water, stierred for a short time at 80° C. and after cooling filtered (removal of the undissolved sulfur). The filtrate was acidified with hydrochloric acid and the separated 5,5'-difluorodiphenyldisulfide-2,2'-diacetic acid filtered and washed with water.

The product was dissolved in 100 ml of acetic acid, 15 g of zinc powder was added and the mixture refluxed for 4 hours. After cooling, the solid was removed by filtration and the filtrate evaporated under reduced pressure. The residue was dissolved by boiling with a slight excess of 5% sodium hydroxide solution, the solution filtered and the filtrate acidified with hydrochloric acid. After standing overnight, the precipitated solid was filtered, added to 120 ml 20% sulfuric acid and 5 g of zinc powder. The mixture was then subjected to steam distillation. From the aqueous distillate, 11.1 g 6-fluoro-1-benzothiephen-2(3H)-one crystallize; the solid was filtered and after drying in vacuo, it recrystallized from petroleum ether. The pure substance melted at 56°–59° C.

The foregoing thiolactone (10.2 g) was dissolved under heat in a solution of 16.8 g anhydrous potassium hydroxide in 80 ml water, and the mixture treated at 80° C. with 0.8 g potassium iodide, a solution of 15.8 g 4-chloronitrobenzene in 160 ml of ethanol. The mixture was refluxed for 12 hours, ethanol distilled off and the residue diluted with water. After standing overnight, the excess of chloronitrobenzene was removed by filtration and the filtrate acidified with hydrochloric acid. Filtration of the precipitated substance, washing with water and drying in vacuo yielded 16.9 g (92%) of crude (4-fluoro-2-[4-nitrophenylthio] phenyl)acetic acid which is practically pure after a single crystallization from ethanol (yield 13.6 g), m.p. 160°–164° C. The analytical sample melted at 162°–164° C.

[4-Fluoro-2-(4-nitrophenylthio)phenyl]acetic acid (17.6 g) was added at 150° C. to polyphosphoric acid, prepared from 60 ml 85% phosphoric acid and 100 g phosphorus pentoxide, and the mixture stirred at 150°–155° C. for two hours. After cooling, it was decomposed by pouring into a mixture of ice and water. The precipitated crude product was filtered and boiled for a short time under stirring with a mixture of a 10% sodium carbonate solution and benzene. It was filtered again, the benzene layer separated and benzene evaporated. The residue was dissolved in a small volume of benzene and the solution chromatographed on a column of 420 g alumina (act. II) Benzene eluted first a small amount of a less polar and high-melting by-product. The elution was continued with benzene and finally with a mixture of benzene and chloroform; 7.25 g of the desired crystalline 3-fluoro-8-nitrodibenzo(b,f)thiepin-10(11H)-one were obtained, m.p. 161°–163° C. (benzene-petroleum ether).

A solution of 6.9 g of the foregoing ketone in 90 ml of dioxane was treated dropwise with a solution of 9.8 g of sodium borohydride in 3 ml of water containing 1 drop of a 20% sodium hydroxide solution. The mixture was stirred for 2 hours at room temperature and after standing overnight, dioxane evaporated. The residue was diluted with water, acidified with hydrochloric acid and the product extracted with chloroform. Processing of the extract and crystallization of the crude product from benzene yielded 4.1 g pure 3-fluoro-8-nitro-10,11-dihydrodibenzo(b,f)thiepin-10-ol, m.p. 133°–135° C.

A solution of 6.8 g of the foregoing alcohol in 100 ml of chloroform was treated with 25 ml of thienyl chloride and the mixture refluxed for 1 hour. After standing overnight, the volatile fractions were evaporated in vacuo and the residue induced to crystallize by mixing with a small quantity of petroleum ether; 6.8 g, m.p. 149°–151° C. The product was the desired 10-chloro-3-fluoro-8-nitro-10,11-dihydrodibenzo(b,f,)thiepin. Its analytical sample melted at 151°–154° C. (benzene-petroleum ether).

EXAMPLE 21

3-Fluoro-10-[4-(2-hydroxyethyl)piperazine]-8-cyano-10,11-dihydrodibenzo(b,f)thiepin and 8-Aminocarbonyl-3-fluoro-10-[4-(2-hydroxyethyl)-piperazine]-10,11-dihydrodibenzo(b,f)thiepin A solution of 10 ml of 1-(2-hydroxyethyl)piperazine in 10 ml of chloroform was treated with 3.6 g of a mixture of 10-chloro-8-cyano-3-fluoro-10,11-dihydrodibenzo(b,f)thiepin and 8-aminocarbonyl-10-chloro-3-fluoro-10,11-dihydrodibenzo(b,f)thiepin and the resulting mixture refluxed for 8 hours. It was then diluted with benzene and the benzene solution washed with water. Standing of the aqueous layer leads to separation of 2.14 g of crystalline 8-aminocarbonyl-3-fluoro-10-[4-(2-hydroxyethyl)piperazine]-10,11-dihydrodibenzo-(b,f)thiepin monohydrate which was recrystallized from aqueous ethanol to melt at 100°–102° C. Neutralization with hydrogen chloride in a mixture of ether and acetone yielded the crystalline dihydrochloride melting at 209°–212° C. (95% ethanol and ether).

The benzene layer, which was washed with water, was shaken with an excess of 5% hydrochloric acid, the aqueous layer separated, made alkaline with aqueous ammonia and the released base isolated by extraction with benzene. Processing of the extract resulted in 1.9 g crude base of 8-cyano-3-fluoro-10-[4-(2-hydroxyethyl)-piperazino]-10,11-dihydrodibenzo(b,f)thiepin which is purified by filtration of a solution in chloroform through a column of 200 g alumina (act. II). The column withholds the remaining more polar 8-aminocarbonyl compound and chloroform eluted only the pure 8-cyano derivative. This was neutralized with methanesulfonic acid in a mixture of ethanol and ether to give the crystalline dimethanesulfonate which is solvated with 1 mol. ethanol and 1 mol. water; m.p. 122°–125° C.

The starting mixture of 8-cyano- and 8-aminocarbonyl-10-chloro-3-fluoro-10,11-dihydrodibenzo(b,f)thiepin was prepared in the following manner starting from [4-fluoro-2-(4-nitrophenylthiophenyl]-acetic acid, the preparation of which is described in the previous Example:

A solution of 19 g [4-fluoro-2-(4-nitrophenylthio)phenyl] acetic acid in 60 ml of acetic acid was slowly added dropwise into a boiling mixture of 300 ml water and 30 g iron powder. The mixture was then stirred and refluxed for 6 hours. After cooling, 200 ml of a 20% sodium hydroxide solution were added, the solution filtered and the filtrate acidified with acetic acid. After standing overnight, the separated product was filtered, washed with a small quantity of water and dried in vacuo. There were obtained 9.5 g of crude [2-(4-aminophenylthio)-4-fluorophenyl]acetic acid melting at 151°–155° C. After a single crystallization from a mixture of benzene and petroleum ether, the product was pure and melted at 154°–156° C.

Polyphosphoric acid was prepared from 150 ml 85% phosphoric acid and 300 g phosphorus pentoxide. It was heated to 125° C. and under stirring, there were added over 45 minutes 20.4 g of the foregoing amino acid. The mixture was stirred for an additional 45 minutes at 125° C. After partial cooling, the mixture was decomposed by pouring on ice, the separated solid filtered, treated with an excess of 5% sodium carbonate solution and extracted with chloroform. Processing of the extract resulted in 16.1 g (85%) crude 8-amino-3-fluorodibenzo(b,f)thiepin-10(11H)-one melting at 198°–204° C. Crystallization from benzene yielded the pure substance with a m.p. of 206°–210° C.

The foregoing aminoketone (11.4 g) was mixed with 45 ml of acetic acid and 45 ml of hydrochloric acid. The resultant suspension of the hydrochloride was cooled to 0° C. and under stirring diazotized with a solution of 4.3 g sodium nitrite in 10 ml water, added dropwise in such a way that the temperature did not surpass 5° C. Under steady cooling, it was stirred for another 1 hour and the resulting solution treated with a solution of 20 g potassium iodide in 200 ml water. The temperature increased to 20° C. and the mixture was stirred without further cooling for 1 hour. After the addition of 200 ml benzene, the stirring was continued for 30 minutes and the mixture allowed to stand overnight. The benzene layer was separated, washed with a 5% sodium hydroxide solution and with a solution of sodium thiosulfate, dried with magnesium sulfate and evaporated. Addition of a small quantity of ethanol induced the crystallization of 11.3 g of the desired 3-fluoro-8-iododibenzo(b,f)thiepin-10(11H)-one melting at 135°–139° C. A further crystallization from ethanol yielded the pure compound with a m.p. of 136°–139° C.

A solution of 11.2 g the foregoing iodoketone in a mixture of 100 ml dioxane and 50 ml ethanol was treated with a solution of 1.15 g of sodium borohydride in 3 ml of water containing 1 drop 20% sodium hydroxide solution and the mixture is stirred without heating for 2 hours. After standing overnight, it was processed as described for analogous compounds in the foregoing Examples. There were obtained 11.2 g (theoretical yield) of the crude 3-fluoro-8-iodo-10,11-dihydrodibenzo(b,f)thiepin-10-ol which crystallized from benzene and in pure state melted at 162° C.

A mixture of 100 ml of dimethylformamide, 9.4 g of 3-fluoro-8-iodo-10,11-dihydrodibenzo(b,f)thiepin-10-ol and 7.2 g of cuprous cyanide was stirred and refluxed for 5 hours. After cooling, it was diluted with 300 ml water, 300 ml benzene added and the mixture filtered with suction. The solid was extracted with a little chloroform and the organic layers combined, dried with magnesium sulfate and evaporated. The residue was dissolved in a small amount of a mixture of benzene and chloroform and the solution chromatographed on a column of 400 g alumina (act. II). It was eluted first with a 1:1 mixture of benzene and chloroform giving 1.15 g of the starting iodo-alcohol. Chloroform alone then eluted 5.18 g (76%) of the desired product, i.e. 8-cyano-3-fluoro-10,11-dihydrodibenzo(b,f)thiepin-10-ol. It was a crystalline substance crystallizing from a mixture of benzene and petroleum ether and melting in the pure state at 130°–131° C.

Calcium chloride (5 g) was added to a solution of 5.0 g of the foregoing cyanoalcohol in 120 ml chloroform and the suspension saturated with hydrogen chloride for 1 hour. After standing overnight, it was filtered and the filtrate evaporated. There were obtained 5.75 g of an oily mixture of 8-cyano- and 8-aminocarbonyl-10-chloro-3-fluoro-10,11-dihydrodibenzo(b,f)thiepin. Addition of ethanol separated crystals melting at 197°–199° C. This fraction, however, was a mixture of the mentioned components.

EXAMPLE 22

8-Acetyl-3-fluoro-10-[4-(2-hydroxyethyl)piperazino]-10,11-dihydrodibenzo(b,f)thiepin A mixture of 2.4 g of 8-acetyl-10-chloro-3-fluoro-10,11-dihydrodibenzo(b,f)thiepin, 5 ml of 1-(2-hydroxyethyl)piperazine and 10 ml of chloroform was refluxed for 7 hours. It was then diluted with benzene, washed thoroughly with water and finally shaken with an excess of 5% hydrochloric acid. The acid aqueous solution of the hydrochloride was separated, made alkaline with a 20% sodium hydroxide solution and the base isolated by extraction with benzene. Processing of the extract yielded 2.6 g (83%) of an oily product which was neutralized with maleic acid in a mixture of acetone and ether. There were obtained 3.9 g bis(hydrogen maleate) melting at 72°–75° C. (acetone-ether).

The starting 8-acetyl-10-chloro-3-fluoro-10,11-dihydrodibenzo(b,f)thiepin is a new compound which may be obtained by the following procedure from 8-amino-3-fluorodibenzo(b,f)thiepin-10(11H)-one, the synthesis of which is described in the foregoing Example.

A solution of 11.5 g 8-amino-3-fluorodibenzo(b,f)thiepin-10(11H)-one in a mixture of 100 ml dioxane and 50 ml ethanol is treated with a solution of 1.9 g sodium borohydride in 5 ml water containing 1 drop 20% sodium hydroxide solution and the resulting mixture stirred and refluxed for 1.5 hour. After standing overnight, the solution is evaporated in vacuo, the residue mixed with water and the product extracted with chloroform. The extract is dried and evaporated and the residue crystallizes after the addition of a small amount of benzene; 11.4 g (98%) of the crude 8-amino-3-fluoro-10,11-dihydrodibenzo(b,f)thiepin-10-ol crystallizing from benzene and melting in the pure state at 128.5°-129° C.

A stirred mixture of 11.2 g of the foregoing aminoalcohol and 40 ml acetic acid is treated with 40 ml hydrochloric acid and the formed suspension of the hydrochloride diazotized at 0°-5° C. with a solution of 3.5 g sodium nitrite in 10 ml water added dropwise. The mixture is stirred and cooled for 1 hour, treated with 1 g of urea and after 10 minutes treated at 0°-5° C. with a solution of 35 g of sodium carbonate in 150 ml water, added over 15 minutes. The resulting mixture is then poured into a suspension of 25 g acetaldehyde semicarbazone in a solution of 25 g sodium acetate trihydrate, 1,5 g cupric sulfate pentahydrate and 0.2 g sodium sulfite in 130 ml water at 5° C. The mixture is stirred for 3 hours without cooling, acidified with 30 ml hydrochloric acid, the precipitated solid is filtered and submitted to hydrolysis by refluxing with a solution of 30 g oxalic acid dihydrate in 200 ml water for 4 hours. After cooling, the separated product is isolated by extraction with chloroform, the extract is dried with magnesium sulfate and chloroform is evaporated. The residue is dissolved in a small amount of a mixture of benzene and chloroform and the solution is chromatographed on a column of 500 g alumina (act. II). Elution with a 1:1 mixture of benzene and chloroform separated the undesired less polar fractions and chloroform alone elutes then 2.88 g of the desired product, i.e. 8-acetyl-3-fluoro-10,11-dihydrodibenzo(b,f)thiepin-10-ol which crystallized from a mixture of benzene and petroleum ether and melts in a pure state at 126.5°-127.5° C.

Calcium chloride (3 g) is added to a solution of 2.35 g foregoing ketoalcohol in 100 ml chloroform and the suspension is saturated with hydrogen chloride for 1 hour at room temperature. After standing for 48 hours, the mixture is filtered and the filtrate evaporated at reduced pressure. The residue is induced to crystallize by mixing with a little of cyclohexane. There are obtained 2.22 g (89%) 8-acetyl-10-chloro-3-fluoro-10,11-dihydrodibenzo(b,f)thiepin which is purified by a further crystallization from cyclohexane and melts at 112°-114° C.

EXAMPLE 23

3-Fluoro-8-isopropyl-10-(4-methylpiperazino)-10,11-dihydrodibenzo(b,f)thiepin

A mixture of 300 ml of acetic acid, 35 g of 3-fluoro-8-isopropyl-10-(4-methylpiperazino)dibenzo(b,f)thiepin and 60 g of zinc dust was stirred and refluxed for 20 minutes. It was then filtered and the filtrate evaporated under reduced pressure. The residue was made alkaline with a 20% sodium hydroxide solution and extracted with benzene. Evaporation of the extract yielded 25 g of an oily base which was neutralized with maleic acid in ethanol. Addition of ether separated the crystalline maleate of m.p. 174°-176° C. which was identical with the product obtained according to Example 1.

The starting 3-fluoro-8-isopropyl-10-(4-methylpiperazine)dibenzo(b,f)thiepin, which is a new compound, is prepared by the following procedure from 3-fluoro-8-isopropyldibenzo(b,f)thiepin-10(11H)-one, the synthesis of which is described in Example 1.

A stirred solution of 8.0 g 3-fluoro-8-isopropyldibenzo(b,f)thiepin-10(11H)-one in 55 ml benzene is treated with a solution of 2.8 g titanium tetrachloride in 14 ml benzene added dropwise. 14 g of 1-methylpiperazine are then slowly added and the mixture refluxed for 16 hours. After cooling, it is decomposed with 80 ml water, added dropwise. 100 ml benzene are then added and the separated solid is filtered. The benzene layer of the filtrate is washed with water, dried with potassium carbonate and evaporated. There are obtained 9.2 g (89%) crude oily base which is neutralized with maleic acid in ethanol. Addition of ether separates the crystalline maleate of 3-fluoro-8-isopropyl-10-(4-methylpiperazino)dibenzo(b,f)thiepin melting at 183°-184° C. with decomposition (ethanol-ether).

EXAMPLE 24

10-(4-Ethylpiperazino)-3-fluoro-8-isopropyl-10,11-dihydrodibenzo(b,f)thiepin

A solution of 4.8 g of 10-(4-acetylpiperazino)-3-fluoro-8-isopropyl-10,11-dihydrodibenzo(b,f)thiepin in 25 ml of tetrahydrofuran was added dropwise to a stirred suspension of 0.6 g of lithium aluminium hydride in 20 ml of tetrahydrofuran and the mixture refluxed for 5 hours. After standing overnight, it was decomposed under stirring by a step-wise addition of 0.6 ml water, 0.7 ml 20% sodium hydroxide solution and 1.7 ml water. After 30 minutes of stirring, the undissolved material was filtered off and washed with tetrahydrofuran. The filtrate was dried with potassium carbonate and evaporated. The residue (4.3 g, 93%) was the crude oily base. Its neutralization with maleic acid in ethanol yielded the crystalline maleate melting at 201°-203° C. (ethanol). The substance was identical with that obtained according to Example 5.

The starting 10-(4-acetylpiperazino)-3-fluoro-8-isopropyl-10,11-dihydrodibenzo(b,f)thiepin, which is a new compound, is prepared by the following procedure from 8-fluoro-8-isopropyl-10-piperazino-1-,11-dihydrodibenzo(b,f)thiepin which is described in Example 4.

A solution of 5.0 g 3-fluoro-8-isopropyl-10-piperazine-10,11-dihydrodibenzo(b,f)thiepin in 20 ml chloroform is stirred and treated dropwise with 2.2 g acetyl chloride. The mixture is then left overnight at room temperature. Then, the separated hygroscopic hydrochloride of the product is filtered with suction, suspended in water and the base released by an excess of 20% sodium hydroxide solution and isolated by extraction with chloroform. Processing of the extract yields 5.4 g (95%) crude base of 10-(4-acetylpiperazino)-3-fluoro-8-isopropyl-10,11-dihydrodibenzo(b,f)thiepin which crystallizes from a mixture of benzene and petroleum ether and melts in a pure state at 164.5°-166° C.

EXAMPLE 25

3-fluoro-10-(4-[2-(4-fluorophenoxy)ethyl]piperazino)-8-isopropyl-10,11-dihydrodibenzo(b,f)thiepin A solution of 3.7 g 3-fluoro-10-[4-(4-fluorophenoxyacetyl)piperazino]-8-isopropyl-10,11-dihydrodibenzo(b,f)thiepin in 10 ml ether is slowly added dropwise to a suspension of 0.5 g lithium aluminium hydride in 20 ml ether. The mixture was refluxed for 4 hours and left overnight. It was then decomposed under stirring by a stepwise addition of 0.4 ml water, 0.6 ml 5 M-NaOH and finally 1.4 ml water. It was stirred for another 30 minutes, the solid filtered off, the filtrate dried with potassium carbonate and evaporated after filtration. The residue was 3.2 g (89%) of the desired oily base which was transformed by neutralization with maleic acid in ethanol to the crystalline dimaleate, m.p. 155.5°–157.5° C. (ethanol). The substance was identical with the product, prepared by a different synthesis according to Example 9.

The used starting 3-fluoro-10-[4-(4'-fluoro-phenosyacetyl)piperazino]-8-isoprophyl-10,11-dihydrodibenzo(b,f)thiepin, which is a new compound, may best be prepared by the following procedure, namely by the reaction of 3-fluoro-8-isopropyl-10-piperazino-10,11-dihydrodibenzo(b,f)thiepin (Example 4) with 4-fluoro-phenoxyacetyl chloride (cf G. Svarnas and W. L. Howard, J. Amer. Chem. Soc. 77, 3924, 1955):

A solution of 2.6 g of 3-fluoro-8-isopropyl-10-piperazino-10,11-dihydrodibenzo(b,f)thiepin in 15 ml of chloroform was stirred and treated dropwise with 1.7 g of 4-fluorophenoxyacetyl chloride and the mixture allowed to stand for 12 hours. It was then diluted with chloroform, washed with a 5% sodium hydroxide solution and water, dried with potassium carbonate, filtered and evaporated. The oily residue (3.7 g, 100%) was the crude 3-fluoro-10-[4-(4-fluorophenoxyacetyl)-piperazino]-8-isopropyl-10,11-dihydrodibenzo(b,f)thiepin which was used in this state for further work.

EXAMPLE 26

3-Fluoro-10-(4-[2-(4-fluorophenylthio)ethyl]-piperazino)-8-isopropyl-10,11-dihydrodibenzo(b,f)thiepin As in the foregoing case, 5.7 g of crude 3-fluoro-10-[4-(4-fluoro-phenylthioacetyl)piperazine]-8-isopropyl-10,11-dihydrodibenzo(b,f)thiepin was reduced with 0.5 g of lithium aluminum hydride in 35 ml of boiling ether for 5 hours. After cooling, decomposition and processing of the ethereal solution, there were obtained 4.9 g (96%) of a crude oily base which was neutralized with maleic acid in ethanol to yield a crystalline maleate with a m.p. of 184°–186.5° C. (ethanol). The substance was identical with the product prepared according to Example 10 by a different method.

The starting 3-fluoro-10-[4-(4-fluorophenylthioacetyl)piperazino]-8-isopropyl-10,11-dihydrodibenzo(b,f)thiepin, which is a new compound, is obtained by the following procedure from the known (4-fluoro-phenylthio)acetic acid (Ju. E. Gerasimenko et al., Zh. Obshch. Khim. 32, 1870, 1962) and from 3-fluoro-8-isopropyl-10-piperazino-10,11-dihydrodibenzo(b,f)thiepin (Example 4):

A mixture of 5.3 g of (4-fluorophenylthio)acetic acid and 6.8 g of thionyl chloride is refluxed for 2 hours. Excess of thionyl chloride is evaporated in vacuo and the residue distilled. There are obtained 5.1 g (88%) of oily (4-fluorophenylthio)acetyl chloride, b.p. 76°–77° C./0.25 Torr.

A reaction of 3.56 g 3-fluoro-8-iospropyl-10-piperazino-10,11-dihydrodibenzo(b,f)thiepin and 2.66 g (4-fluorophenylthio)acetyl chloride in 20 ml of chloroform was carried out as in the foregoing Example. There were obtained 5.2 g (100%) of crude oily 3-fluoro-10-[4-(4-fluorophenylthioacetyl)piperazino]-10,11-dihydrodibenzo(b,f)thiepin which was used for reduction in this state.

EXAMPLE 27

3-Fluoro-8-isopropyl-10-piperazino-10,11-dihydrodibenzo(b,f)thiepin

A mixture of 26.8 g of 10-(4-ethoxycarbonyl-piperazino)-3-fluoro-8-isopropyl-10,11-dihydrodibenzo(b,f)thiepin, 10 6 of potassium hydroxide and 20 ml of ethanol were stirred and heated under reflux for 2 hours in a bath of 120° C. After cooling, the mixture was diluted with some water and the product extracted with benzene. The extract was washed with water, dried with potassium carbonate and evaporated. The base was obtained in a yield of 20 g (86%); it crystallized from cyclohexane and melted at 122°–124° C. Neutralization with maleic acid in 95% ethanol and addition of ether yields a crystalline maleate crystallizing from a mixture of 95% ethanol and ether as a hemihydrate, m.p. 162° C. The substance was identical with the product obtained according to Example 4 by a different method.

The used starting 10-(4-ethoxycarbonylpiperazino)-3-fluoro-3-isopropyl-10,11-dihydrodibenzo(b,f)thiepin is a new compound which may be prepared by the reaction of 10-chloro-3-fluoro-8-isopropyl-10,11-dihydrodibenzo(b,f)thiepin (Example 1) with 1-(ethoxycarbonyl)piperazine:

A mixture of 20 g of 10-chloro-3-fluoro-8-isopropyl-10,11-dihydrodibenzo(b,f)thiepin, 21 g of 1-(ethoxycarbonyl)piperazine and 30 ml of chloroform is refluxed for 5 hours. After cooling, it is diluted with chloroform, the solution thoroughly washed with water, dried with potassium carbonate and after filtration evaporated under reduced pressure. The residue (27 g, 96%) is a crude glassy 10-(ethoxycarbonylpiperazino)-3-fluoro-8-isopropyl-10,11-dihydrodibenzo(b,f)thiepin which is used for hydrolysis in this state without further purification.

EXAMPLE 28

10-(4-[2-(1,3-Dioxolan-2-yl)ethyl]piperazino)-3-fluoro-8-isopropyl-10,11-dihydrodibenzo(b,f)thiepin A mixture of 3.5 g of 3-fluoro-8-isopropyl-10-piperazino-10,11-dihydrodibenzo(b,f)thiepin (Examples 4 and 27), 2.1 g of 2-(2-chloroethyl)-1,3-dioxolane (R. Ratovis and J. R. Boissier; Bull, Soc. Chim. France 1966, 2963), 1.4 g of anhydrous potassium carbonate and 5 ml of dimethylformamide was stirred and refluxed for 5 hours. After cooling, it was diluted with 30 ml water and extracted with chloroform. The extract was washed with water, dried with sodium sulfate and evaporated in vacuo. The residue was chromatographed on a column of 200 g alumina (act.II). With benzene, there were eluted 2.6 g of the desired homogeneous base which was neutralized with maleic acid in ethanol to give the dimaleate. After crystallization from ethanol, it was pure and melted at 127°–129° C. The substance was identical with the product obtained according to Example 13 in a different way.

EXAMPLE 29

10-[4-(2-Acetoxyethyl)piperazino]-3-fluoro-8-isopropyl-10,11-dihydrodibenzo(b,f)thiepin A solution of 1.0 g of 3-fluoro-10-[4-(2-hydroxyethyl)piperazino]-8-isopropyl-10,11-dihydrodibenzo(b,f)thiepin base (Example 3) in 5 ml chloroform was treated with 0.5 g acetic anhydride and the mixture allowed to stand overnight at room temperature. It was then diluted with 20 ml of chloroform, washed with water and with ice-cold sodium hydroxide solution, dried with potassium carbonate, and the chloroform evaporated under reduced pressure. The remaining oil (1.1 g, 100%) was dissolved in 3.5 ml of acetone and the solution neutralized under heating with 0.6 g maleic acid. On cooling, 1.3 g (77%) of dimaleate crystallized which was then recrystallized from acetone and melted at 153°–155.5° C.; it was identical with the product obtained by a different way according to Example 14.

EXAMPLE 30

10-[4-(2-Decanoyloxyethyl)piperazino]-3-fluoro-8-isopropyl-10,11-dihydrodibenzo(b,f)thiepin A mixture of 4.0 g of 3-fluoro-10-[4-(2-hydroxyethyl)piperazino]-8-isopropyl-10,11-dihydrodibenzo(b,f)thiepin (Example 2), 5.5 g of decanoic acid and 40 ml of xylene was slowly distilled over 7 hours and the distillate continually substituted with pure xylene so that the volume of the mixture remained approximately constant. The mixture was then diluted with 50 ml benzene, the solution washed with an ice-cold 5% sodium hydroxide solution, dried with potassium carbonate and evaporated. The residue (5.3 g, 96%) was the crude oily ester which by neutralization with maleic acid in acetone yielded a dimaleate, m.p. 112°–113° C. (acetone). The compound was identical with the product obtained by a different way according to Example 15.

EXAMPLE 31

3-Fluoro-8-isopropyl-10-(4-[2-(3,4,5-trimethoxybenzoyloxy)ethyl]piperazino)-10,11-dihydrodibenzo(b,f)thiepin A solution of 5.7 g of 3-fluoro-10-[4-(2-hydroxyethyl)piperazino]-8-isopropyl-10,11-dihydrodibenzo(b,f)thiepin (Example 2) in 20 ml of chloroform was treated with 5.2 g of 3,4,5-trimethoxybenzoyl chloride and after its dissolution, the mixture left overnight at room temperature. It was then decomposed with water and then diluted with chloroform and washed with an ice-cold 5% sodium hydroxide solution, dried with potassium carbonate and the chloroform evaporated. The remaining oil (8.4 g, 100%) was the crude ester which was neutralized with oxalic acid in ethanol to yield an oxalate crystallizing from aqueous ethanol and melting at 188°–192° C. with decomposition. The compound is identical with the product obtained by a different way according to Example 16.

EXAMPLE 32

3-Fluoro-8-hydroxy-10-(4-methylpiperazino)-10,11-dihydrodibenzo(b,f)thiepin

A solution of 4.0 g of 3-fluoro-8-methoxy-10-(4-methylpiperazino)-10,11-dihydrodibenzo(b,f)thiepin in 40 ml of pure chloroform was stirred and treated dropwise over 15 minutes at 15° C. with a solution of 8.42 g of boron tribromide in 20 ml of pure chloroform; the mixture was then stirred for 5 hours at room temperature. After standing overnight, chloroform was evaporated under reduced pressure, the residue dissolved in 120 ml of ethanol and 45 ml water and the mixture stirred and refluxed for 5 hours. After standing overnight, the separated solid was filtered with suction, washed with aqueous ethanol, suspended in 100 ml of 5% sodium carbonate solution and the released base isolated by extraction with chloroform. The extract was dried with sodium sulfate and chloroform evaporated. The residue crystallized after treatment with petroleum ether; 2.44 g (64%) of crude phenolic base with a m.p. of 221°–224° C. The pure substance was obtained by recrystallization from ethanol and melted at 234°–234.5° C. Neutralization with maleic acid in ethanol yielded a maleate which crystallized from ethanol and melted at 175° C.

The starting 3-fluoro-8-methoxy-10-(4-methylpiperazino)-10,11-dihydrodibenzo(b,f)thiepin is a new compound which is obtained like the analogous substance, described in Example 8, i.e. from (4-fluoro-2-iodophenyl)acetic acid (Example 17) and the known 4-methoxythiophenol via the following intermediates:

[4-Fluoro-2-(4-methoxyphenylthio)phenyl] acetic acid, m.p. 110° C. (aqueous ethanol);

3-Fluoro-8-methoxydibenzo(b,f)thiepin-10(11H)-one, m.p. 129°–130° C. (ethanol);

3-Fluoro-8-methoxy-10,11-dihydrodibenzo(b,f)thiepin-10-ol, m.p. 118° C. (ethanol);

10-Chloro-3-fluoro-8-methoxy-10,11-dihydrodibenzo(b,f)thiepin, m.p. 129° C. (cyclohexane).

The base of 3-fluoro-8-methoxy-10-(4-methylpiperazino)-10,11-dihydrodibenzo(b,f)thiepin is a crystalline solid melting at 81° C. (petroleum ether). Its neutralization with maleic acid affords a maleate crystallizing from ethanol and melting at 172° C.

EXAMPLE 33

8-Amino-3-fluoro-10-[4-(2-hydroxybutyl)piperazino]-10,11-dihydrodibenzo(b,f)thiepin A solution of 2.6 g of 3-fluoro-10-[4-(2-hydroxyethyl)piperazino]-8-nitro-10,11-dihydrodibenzo(b,f)thiepin (Example 20) in 25 ml ethanol was treated with 0.4 g of charcoal, 2.5 ml of 100% hydrazine hydrate and 0.1 g of ferric chloride in 5 ml of ethanol and the mixture refluxed for 6 hours. Ethanol was evaporated in vacuo and the residue transformed with dilute hydrochloric acid to a solution of the hydrochloride. The base was released by treatment with a 20% sodium hydroxide solution and isolated by extraction with other. After drying the extract with potassium carbonate, ether was evaporated and the residue transformed by treatment with methane sulfonic acid in a mixture of 95% ethanol and ether to a crystalline salt, identified as the tri(methanesulfonate)dihydrate, m.p. 184°–186° C. Considered as cataleptic were those animals which persisted for a period of 5 seconds in the position with crossed paws. The compounds under test were administered orally to groups of 10 animals each, and the catalepsy was estimated one hour later and thereafter at half-hour intervals over a period of an additional 5 hours. From the optimum values obtained during the experiment, the respective median effective doses $ED_{50}$ were calculated. The cataleptic effect was thereupon followed each 24 hours until its complete disappearance.

(2) The anti-apomorphine effect was estimated in male rats by the method of Janssen and collaborators (Arzneim.-Forsch. 10, 1003, 1960; ibid. 17, 841, 1967)/ The individual doses were administered orally to rat groups of 10 animals each, followed—after 4 hours and once again after 24 hours—by intravenous injection of apomorphine in single doses of 1.25 mg/kg. The chewing behavior and motility of the test animals (caged separately) were observed, and the percentual depression (in comparison with the controls, whose response was taken equal to 100%) of the apomorphine chewing and agitation at the two dosage time intervals was evaluated.

(3) The anti-apomorphine effect was also determined in beagle dogs (of 5–12 kg body weight) with experimental vomiting reflex produced by subcutaneous injection of apomorphine hydrochloride dosed at 0.31 mg/kg level, dissolved in a volume of 0.1 mg/kg. Four days after the verification of the reactivity of the test dogs to apomorphine (the vomiting response to the latter substance reliably occurred in all of the animals), an oral dose of the compound under test was administered. The average vomiting frequency and the percentual ratio of animals with complete blockade of emesis was statistically evaluated.

The compounds of the invention may be employed as highly potent antipsychotics in the therapy of schizophrenic diseases. When an immediate onset of the action is required, they are administered orally or parenterally (subcutaneously, intramuscularly or also intravenously) in single doses not exceeding 10 mg daily. The oral application may occur either in the form of tablets or drops of aqueous solutions of water-soluble salts of the compounds of the invention. For the parenteral administration, too, aqueous solutions of such soluble salts are employed. In the maintenance therapy, where protracted duration of the effects over longer periods of time is desired, the substances can advantageously be administered intramuscularly in the form of solutions of the respective bases in vegetable or synthetic oils. In these cases, the therapeutic effects of a single 10–25 mg dose of the substance subsist over a period of one or even several weeks.

For sake of evidencing the pharmacological effects of the compounds of the invention, the respective properties of several typical examples of these substances are demonstrated herein below. Initially, the pharmacological methods used in testing these substances are reviewed.

Acute toxicity was determined in female mice, in groups of ten animals. The mortality was observed over 7 days following the oral administration. The results are presented herein below by indicating the respective median lethal doses $LD_{50}$ in mg/kg.

For the evaluation of psychotropic activity, the following methods were employed.

(1) The catalepsy was evaluated in female rats, by the method of Boissier and Simon (Therapie 18, 1257, 1963). Assay counts were made after 24, 48 and 96 hours upon the administration of the tested substance, repeating each time the above-indicated apomorphine hydrochloride dosage.

(4) Analogous determination of the anti-apomorphine effect of the compounds in dogs was performed upon the intramuscular application, in the form of their solutions in oil, using the assay technique of Janssen and Miemegeers (Arzneim.-Forsch. 9, 765, 1959). The evaluation was made at successive intervals of one week.

(5) The interfering effect on the motor coordination, as a criterion of the central depressant activity, was followed in female mice by the common rota-rod test technique (cf., e.g., J. Metysova et al., Arzneim-Forsch. 13, 1039, 1963). The ability of the animals, to maintain themselves for one minute on an axially rotating horizontal rod was estimated in 10-membered groups of the animals. The intervals between the substance dosage and the motor coordination observation were 15, 30, 45, 60, 90 and 120 minutes, and subsequently 24, 48 and if necessary also 72 hours, and median effective doses ($ED_{50}$) in the period of the optimum action of the compounds under test were calculated.

(6) The inhibitory effect on the locomotor activity of mice, as another criterion of the central depressant activity of the compounds, was determined by the photocell method according to Dews (Brit. J.Pharmacol. 8, 46, 1953). The mice were placed in groups of three, and 5 groups were used for each dosage level tested. The compounds were administered orally, and their effect on the locomotor activity was observed after one hour upon the application and thereafter repeatedly at 24 hours intervals until disappearance. The results were expressed as the respective dose which lowered the average control value by 50% ($D_{50}$) and the corresponding percentual depression of the locomotor activity (controls=100%).

For comparative purposes, the above assay results obtained with the use of the afore-mentioned reference compounds are first summarized hereinbelow.

Chlorpromazine: Toxicity, $LD_{50}=198$ mg/kg. Catalepsy, $ED_{50}=16.0$ mg/kg. Anti-apomorphine effect in rats—a dose of 69 mg/kg lowers the apomorphine chewing to 50% against the control. Motor corrdination, $ED_{50}=8.2$ mg/kg. Locomotor activity, $D_{50}=4.8$ mg/kg.

Octoclothepin: Toxicity, $LD_{50}=78$ mg/kg. Catalepsy, $ED_{50}=4.3$ mg/kg. Anti-apomorphine effects in rats—a dose of 10.8 mg/kg lowers the apomorphine chewing to 50% against the control. Motor coordination, $ED_{50}=2.2$ mg/kg. Locomotor activity, $D_{50}=1.1$ mg/kg.

The effects of these two reference compounds do not evidence any sign of prolongation, i.e., the responses in all the enumerated tests disappear before 24 hours after administration.

Several typical compounds of the invention gave the following results:

8-Ethyl-3-fluoro-10-(4-methylpiperazino)-10,11-dihydrodibenzo(b,f)thiepin (tested as maleate, compound 12330):

Toxicity, $LD_{50}=50$ mg/kg. Catalepsy, $ED_{50}=0.88$ mg/kg. Anti-apomorphine effect in rats—a dose of 2.5 mg/kg lowers the apomorphine chewing as well as agitation to 16% against the control. Motor coordination, $ED_{50}=0.36$ mg/kg. After 24 hours, the ataxia still subsists in 70% of the animals. Locomotor activity, $D_{50}=0.17$ mg/kg.

3-Fluoro-8-isopropyl-10-(4-methylpiperazino)-10,11-dihydrodibenzo(b,f)thiepin(tested as maleate, compound 10661):

Toxicity, $LD_{50}=57$ mg/kg. Catalepsy, $ED_{50}=2.0$ mg/kg. In this test, the compound was administered at dosage levels ranging from 0.5 to 5.0 mg/kg. Upon higher doses, the catalepsy subsisted after 24 hours in 40% of the animals. Anti-apomorphine effect in rats—a dose of 2.5 mg/kg lowers the apomorphine chewing as well as agitation to 11% against the control. After 24 hours, the chewing is still lowered to 90% whereas the agitation is not affected any more. Motor coordination, $ED_{50}=0.7$ mg/kg (maximum effect occurs after 2 hours after administration). In this test, the compound was administered at dosage levels ranging from 0.25 to 2.5 mg/kg. Upon higher doses, the ataxia subsisted after 24 hours following the application in 60% of the animals, and after 36 hours it still subsisted in 20% of the animals under test. Locomotor activity, $D_{50}=0.41$ mg/kg. A dose of 1 mg/kg maintains a lowered locomotor activity after 12 hours at 24%, after 24 hours at 36%, and after 48 hours at 70% level against the control.

3-Fluoro-10-[4-(2-hydroxyethyl)piperazino]-8-isopropyl-10,11-dihydrodibenzo(b,f)thiepin (tested as bis(-hydrogenmaleate) hemihydrate, compound 10662):

Toxicity, $LD_{50}=230$ mg/kg. Catalepsy, $ED_{50}=2.0$ mg/kg. In this test, the compound was administered at dosage levels ranging from 0.5 to 5.0 mg/kg. Upon higher doses, the catalepsy subsisted after 24 hours in 60% of the animals. Anti-apomorphine effect in rats—a dose of 5.0 mg/kg lowers the apomorphine chewing to 16% and the agitation to 15% against the control. After 24 hours, the chewing and the agitation are still lowered at 80 and 81% level, respectively. Anti-apomorphine effect in dogs—an oral dose of 1 mg/kg very efficien the depresses the apomorphine emesis during 24 hours upon the administration, the vomiting frequency depression still being statistically significant after 48 hours. The anti-apomorphine effect disappears before the fifth day following the application. The percentual rate of the animals with complete blockade of the apomorphine emesis is statistically significant over the period of 24 hours upon the administration. Motor coordination, $ED_{50}=1.3$ mg/kg (maximum effect occurs after 2 hours upon the application). In this test, the compound was administered at dosage levels ranging from 0.1 to 1.0 mg/kg. In case of higher doses, the ataxia subsisted after 24 hours following the application in 50% of the animals. Locomotor activity, $D_{50}=0.97$ mg/kg. A dose of 1.0 mg/kg maintains a lowered locomotor activity after 12 hours at 55%, after 24 hours further lowering to 33% occurs, and after 48 hours, the locomotor activity is still lowered to 72% against the control. A dose of 2.0 mg/kg maintains a lowered locomotor activity after 12 hours at 9%, after 24 hours at 20%, and after 48 hours at 54% level against the control. Similarly, a dose of 4.0 mg/kg maintains a lowered locomotor activity after 24 hours at 10% and after 48 hours at 28% level against the control.

10-[4-(2-Decanoyloxyethyl)piperazino]-3-fluoro-8-isopropyl-10,11-dihydrodibenzo(b,f)thiepin (compound 13707, administered in a Miglyol solution containing 25 mg of the base per ml of the solution):

Anti-apomorphine effect in rats—an intramuscular dose of 25 mg/kg suppresses significantly the apomorphine chewing as well as agitation until the seventh day following the application. On the ninth day, the depressant effect on the motility is still significant, and this action does not disappear before the 13th day. As to the anti-apomorphine effect in dogs, the intramuscular injection of a single dose of 5 mg/kg results in complete blockade of the apomorphine emesis, which—in the majority of the animals of the test group—subsists over a period of 4 weeks. In 20% of the treated animals under test, this blockade was observed even after 6 weeks upon the administration.

8-Ethoxy-8-fluoro-10[4-methylpiperazino]-10,11-dihydrodibenzo(b,f)thiepin (tested as maleate, compound 12354):

Toxicity, $LD_{50}=91$ mg/kg. Catalepsy, $ED_{50}=2.0$ mg/kg. Anti-apomorphine effect in rats—a dose of 5 mg/kg lowers the apomorphine chewing to 72% and the agitation to 75% against the control. Motor coordination, $ED_{50}=0.36$ mg/kg. Upon higher doses, the ataxy still subsists after 24 hours in 30% of the animals. Locomotor activity, $D_{50}=0.29$ mg/kg. On administering higher doses (0.8 and 1.6 mg/kg), the effect is still significant after 24 hours upon the application.

3-Fluoro-8-hydroxy-10-[4-methylpiperazino]-10,11-dihydrodibenzo(b,f)thiepin (tested as maleate, compound 12394):

Catalepsy, $ED_{50}=5.4$ mg/kg. On higher doses, the catalepsy in 20% of the animals subsists longer than 24 hours upon the administration, Motor coordination, $ED_{50}=0.72$ mg/kg.

8-(Ethylthio)-3-fluoro-10[4-methylpiperazino]-10,11-dihydrodibenzo(b,f)thiepin (tested as maleate, compound 12329):

Toxicity, $LD_{50}=67$ mg/kg. Catalepsy, $ED_{50}=5.4$ mg/kg. Upon higher doses, the catalepsy subsists after 24 hours in 40% of the animals. Anti-apomorphine effect in rats—a dose of 10 mg/kg lowers the apomorphine chewing to 11% and the agitation to 19% against the control. Motor coordination, $ED_{50}=0.68$ mg/kg. On higher doses, the ataxia subsists after 24 hours in 70% of the animals. Locomotor activity, $D_{50}=0.52$ mg/kg. Upon administering higher doses (0.8 and 1.6 mg/kg), a significant inhibition of the locomotor activity still subsists after 24 hours.

8-Acetyl-3-fluoro-10[4-(2-hydroxyethyl)piperazino]-10,11-dihydrodibenzo(b,f)thiepin (tested as bis(hydrogenmaleate), compound 12468):

Catalepsy, $ED_{50}=1.45$ mg/kg. Motor coordination, $ED_{50}=0.4$ mg/kg. On higher doses, the ataxia in 30% of the animals is protracted beyond the period of 24 hours.

Also numerous compounds of the invention evidence remarkable antimicrobial effects in standard in-vitro tests. Especially typical is their inhibitory activity towards Mycobacterium tuberculosis H37Rv (serial numbers of the compounds and the respective minimum inhibiting concentrations in μg/ml are indicated): 12330, 1.5; 12354, 6.2; 12329, 3.12; 12468, 25. From among these compounds, a particularly interesting example as to its antimicrobial activity is compound 12470, i.e., 3-fluoro-8-isopropyl-10-piperazino-10,11-dihydrodibenzo(b,f)thiepin (tested as maleate hemihydrate). Test microorganisms used and the respective minimum inhibiting concentrations in μg/ml are indicated: *Streptococcus beta-haemolyticus* 6.25, *Streptococcus faecalis* 6.25, *Staphylococcus pyogenes aureus* 6.25. *Escherichia coli* 6.25, *Proteus vulgaris* 25, *Mycobacterium tuberculosis* 6.25, *Saccharomyces pastorianus* 12.5, *Trichophyton mentagrophytes* 12.5, *Candida albicans* 50. It is evident that this compound 12470 has a broad spectrum of the antimicrobial activity.

As it has already been stated hereinbefore, the present invention also provides addition salts of the compounds of the general formula I with pharmaceutically utilizable inorganic or organic acids. For oral application, comparatively low water-solubility of the salts is not disadvantageous; preferable salts in this respect are the maleates. For the preparation of aqueous solutions for parenteral application, the corresponding methanesulfonates, which are readily water-soluble, are of advantage. In cases where the salts are very sparingly soluble in water, the respective bases can be administered, conveniently in the form of their solutions in oils.

What is claimed is:

1. 3-Fluoro-8-isopropyl-10-[4-methylpiperazino]-10,11-dihydrodibenzo(b,f)thiepin.

2. The maleate of the composition of claim 1.

3. 3-Fluoro-10-[4-(2-hydroxyethyl)piperazino]-8-isopropyl-10,11-dihydrodibenzo(b,f)thiepin.

4. The dimaleate of the composition of claim 3.

5. 10-[4-(Deconoyloxyethyl)piperazino]-3-fluoro-8-isopropyl-10,11-dihydrodibenzo(b,f)thiepin.

6. 3-Fluoro-8-isopropyl-10-piperazino-10,11-dihydrodibenzo(b,f)thiepin.

7. The maleate of the composition of claim 6.

* * * * *